US006695952B1

United States Patent
Rüdinger et al.

(10) Patent No.: US 6,695,952 B1
(45) Date of Patent: Feb. 24, 2004

(54) METHOD FOR THE SEPARATION OF AND PURIFICATION OF AN AQUEOUS MIXTURE CONSISTING OF THE MAIN COMPONENTS ACETIC ACID AND FORMIC ACID

(75) Inventors: Christoph Rüdinger, Starnberg (DE); Harald Herbert Voit, Reischach (DE); Michael Hallmann, Hochburg-Ach (AT); Mehmet Günaltay, Emmerting (DE); Barbara Geborene Neé Reil Wild, Emmerting (DE); Hans Jürgen Eberle, München (DE)

(73) Assignee: Consortium fur Elektrochemische Industrie GmbH, München (DE)

( * ) Notice: Subject to any disclaimer, the term of this patent is extended or adjusted under 35 U.S.C. 154(b) by 44 days.

(21) Appl. No.: 10/030,533

(22) PCT Filed: Jun. 29, 2000

(86) PCT No.: PCT/EP00/06083

§ 371 (c)(1),
(2), (4) Date: Jan. 9, 2002

(87) PCT Pub. No.: WO01/07390

PCT Pub. Date: Feb. 1, 2001

(30) Foreign Application Priority Data

Jul. 22, 1999 (DE) .......................... 199 34 411

(51) Int. Cl.$^7$ .......................... B01D 11/00; C07C 51/44; C07C 53/02

(52) U.S. Cl. .............................. 203/15; 203/16; 203/45; 203/46; 203/78; 203/99; 203/DIG. 19; 562/608; 562/609

(58) Field of Search .............................. 203/43–46, 99, 203/DIG. 19, 15–16, 78, 77, 73–75; 562/608, 513, 609

(56) References Cited

U.S. PATENT DOCUMENTS 3,718,545 A * 2/1973 Horlenko ...................... 203/15
4,081,355 A * 3/1978 Preusser et al. ............. 208/313

(List continued on next page.)

FOREIGN PATENT DOCUMENTS

| CA | 1 238 919 | 7/1988 |
| DE | 1204214 | 6/1966 |

(List continued on next page.)

OTHER PUBLICATIONS

English Derwent Abstract AN 1996–078095 corresponding to DE 44 26132.
Process Economics Program, Report No. 37A (1973), Stanford Research Institute.
Hunsmann and Simmrock, Chemie–Ing.–Tech., 38, 1966.

*Primary Examiner*—Virginia Manoharan
(74) *Attorney, Agent, or Firm*—Collard & Roe, P.C.

(57) ABSTRACT

A method for the separation and purification of an aqueous mixture of main components, namely acetic acid and formic acid and non-volatiles by extraction, uses a solvent in a circulatory system. A raffinate stream is mixed with the larger proportion of water from a solvent stripper column (11) for the removal of water. The extraction stream is introduced into a solvent distillation column (8), from which in a first step involving the use of a mixture (A) containing a larger proportion of the solvent is separated out via a header and a mixture (B) of formic acid, water and solvent is separated out via a side offtake and a mixture (C) of acetic acid and non-volatiles is also separated out. A mixture (B) is introduced into a formic acid distillation column (4) for further processing, and a mixture (C) is introduced into an acetic acid distillation column (5), and purified acetic acid is subsequently isolated in the acetic acid distillation column (5) from the header. Pure formic acid is isolated at the settling basin of the formic acid distillation column (4).

13 Claims, 4 Drawing Sheets

U.S. PATENT DOCUMENTS

| | | | |
|---|---|---|---|
| 4,088,676 A | * | 5/1978 | Hofen et al. .................... 562/6 |
| 4,262,140 A | | 4/1981 | Bott et al. |
| 4,661,208 A | * | 4/1987 | Honma et al. ................. 203/15 |
| 4,735,690 A | * | 4/1988 | Berg et al. ..................... 203/51 |
| 4,877,490 A | | 10/1989 | Berg et al. |
| 4,935,100 A | | 6/1990 | Berg et al. |
| 5,006,205 A | | 4/1991 | Berg et al. |
| 5,173,156 A | | 12/1992 | Berg et al. |
| 5,633,402 A | | 5/1997 | Berg |
| 5,662,780 A | | 9/1997 | Sasaki et al. |

FOREIGN PATENT DOCUMENTS

| | | |
|---|---|---|
| DE | 4426132 | 1/1996 |
| DE | 19610356 | 4/1997 |
| EP | 0 012 321 | 8/1981 |
| EP | 0156 309 | 6/1989 |
| EP | 0732320 | 9/1996 |
| EP | 0635474 | 4/1999 |
| GB | 727078 | 3/1955 |
| GB | 788931 | 1/1958 |

* cited by examiner

METHOD FOR THE SEPARATION OF AND PURIFICATION OF AN AQUEOUS MIXTURE CONSISTING OF THE MAIN COMPONENTS ACETIC ACID AND FORMIC ACID

CROSS REFERENCE TO RELATED APPLICATIONS

Applicant claims priority under 35 U.S.C. §119 of German Application No. 199 34 411.6 filed Jul. 22, 1999. Applicant also claims priority under 35 U.S.C. 365 of PCT/EP00/06083 filed Jun. 29, 2000. The international application under PCT article 21(2) was not published in English.

BACKGROUND OF THE INVENTION

1. Field of the Invention

The invention relates to a process for the separation and purification of an aqueous reaction mixture comprising the main components acetic acid and formic acid.

2. The Prior Art

The preparation of acetic acid by catalytic oxidation of saturated and/or unsaturated hydrocarbons, for example the gas-phase oxidation of $C_4$-hydrocarbons, results in formation of product streams comprising as main components acetic acid, formic acid and water in varying proportions.

To work them up further, these product streams have to be separated into their individual components. Separation of a ternary acid/water mixture comprising acetic acid, formic acid and water into its pure components by distillation, for example, presents considerable problems since the system contains not only the binary water/formic acid maximum azeotrope but also a ternary water/formic acid/acetic acid saddle azeotrope.

If such a mixture has a high water concentration, separation by distillation has a tremendous additional energy requirement since all the water has to be distilled off at the top of a column as lowest-boiling component.

For the separation of aqueous mixtures having an acetic acid content of >60% by weight and a formic acid content of 5% by weight, Hunsmann and Simmrock (Chemie-Ing.-Tech., 38, 1966) recommend the use of azeotropic distillation for making the separation easier and for reducing the energy required. As azeotropic entrainer for the removal of water, ethyl n-butyl ether is proposed. The azeotrope of water and entrainer boils at about 91° C. and contains about 10% by weight of water. The entrainer ethyl n-butyl ether forms no azeotrope with formic acid and acetic acid.

For separating off formic acid, DE-A 1204214 recommends azeotropic rectification using n-butyl chloride as entrainer. The disadvantage of this process is the use of chlorinated hydrocarbons as entrainer.

U.S. Pat. No. 5,633,402 discloses a process for the separation of binary mixtures of formic acid and acetic acid by means of azeotropic distillation. Methyl formate is used as entrainer for the formic acid. Removal of water is not described in this process.

DE-A 4426132, EP-A 0635474, DE-A 19610356 (U.S. Pat. No. 5,662,780) disclose various processes for the purification and dewatering of acetic acid by means of azeotropes with various entrainers. However, none of these processes describes the dewatering of a mixture of acetic acid and formic acid.

U.S. Pat. No. 5,173,156, U.S. Pat. No. 5,006,205, U.S. Pat. No. 4,877,490 and U.S. Pat. No. 4,935,100 disclose processes for the dewatering of formic acid by means of extractive rectification. Entrainers mentioned here are, for example, cyclohexanone, oxalic acid, decanoic acid and methyl salicylate.

EP-A 156309 (CA-A 1238919) and EP-A 12321 (U.S. Pat. No. 4,262,140) describe the dewatering of formic acid by extractive rectification using carboxamides as auxiliaries. However, none of these processes describes the dewatering of a mixture of acetic acid and formic acid.

The "Process Economics Program" Report No. 37A (1973) of the Stanford Research Institute discloses a process for the separation of an aqueous mixture comprising about 42% by weight of acetic acid and 2% by weight of formic acid. In this process, the aqueous mixture is concentrated by countercurrent extraction with diisopropyl ether. In the dewatering and solvent recovery column, the water is distilled off at the top as an azeotrope of water and diisopropyl ether. The bottom product, namely a mixture of acetic acid and formic acid containing about 0.12% by weight of water, is fractionated further by azeotropic rectification. Benzene is used as entrainer for the formic acid. A great disadvantage of this process is the low quality of the formic acid separated off, which still contains about 1% by weight of acetic acid, about 2% by weight of water and about 7% by weight of benzene. The use of benzene in this process and the residual benzene content in the formic acid make this process unattractive.

All the processes known from the prior art are either only suitable for satisfactorily separating binary mixtures such as acetic acid/water, formic acid/water and acetic acid/formic acid or only economically applicable to aqueous acid mixtures in which a high concentration of acid (>60% by weight) is present. Furthermore, some of the known processes are no longer acceptable from the point of view of today's safety and environmental standards because of their use of benzene or chlorinated hydrocarbons.

SUMMARY OF THE INVENTION

It is therefore an object of the invention to provide a process for the separation of a ternary, aqueous mixture of acids into its pure components, which process does not have the disadvantages mentioned in the discussion of the prior art.

It has now been found that the separation and purification of a mixture comprising the main components acetic acid, formic acid, water and high boilers (hereinafter referred to as crude acid) can be carried out particularly readily if the mixture is extracted by means of a solvent in a circulation process in a first step and the extract stream consisting predominantly of solvent, acetic acid, formic acid, high boilers and water is subsequently fractionated in a sequence of distillation steps into the constituents solvent which is recirculated to the extraction, water, formic acid, acetic acid and high boilers, and the raffinate stream is freed of solvent in a further distillation step by means of a solvent stripping column.

The invention provides a process for the separation and purification of an aqueous mixture comprising the main components acetic acid, formic acid and high boilers by extraction with a solvent in a circulation process, which comprises feeding the raffinate stream containing a major part of the water to a solvent stripping column (11) for removal of the water and conveying the extract stream to a solvent distillation column (8) from which, in a first step, a mixture (A) comprising the major part of the solvent (line (1)) is separated off via the top and a mixture (B) comprising formic acid, water and solvent is separated off via a side offtake and a mixture (C) comprising acetic acid and high boilers is separated off via the bottom, and, for further processing, conveying (line (2)) the mixture (B) to a formic acid distillation column (4) and conveying (line (3)) the mixture (C) to an acetic acid distillation column (5), subsequently isolating the pure acetic acid at the top of the acetic acid distillation column (5), isolating the pure formic acid at the bottom of the formic acid distillation column (4) and at the top taking off a mixture of solvent and water which, together with the mixture (A) after separating off the water present, is recirculated to the extractor (7).

Figure 1:
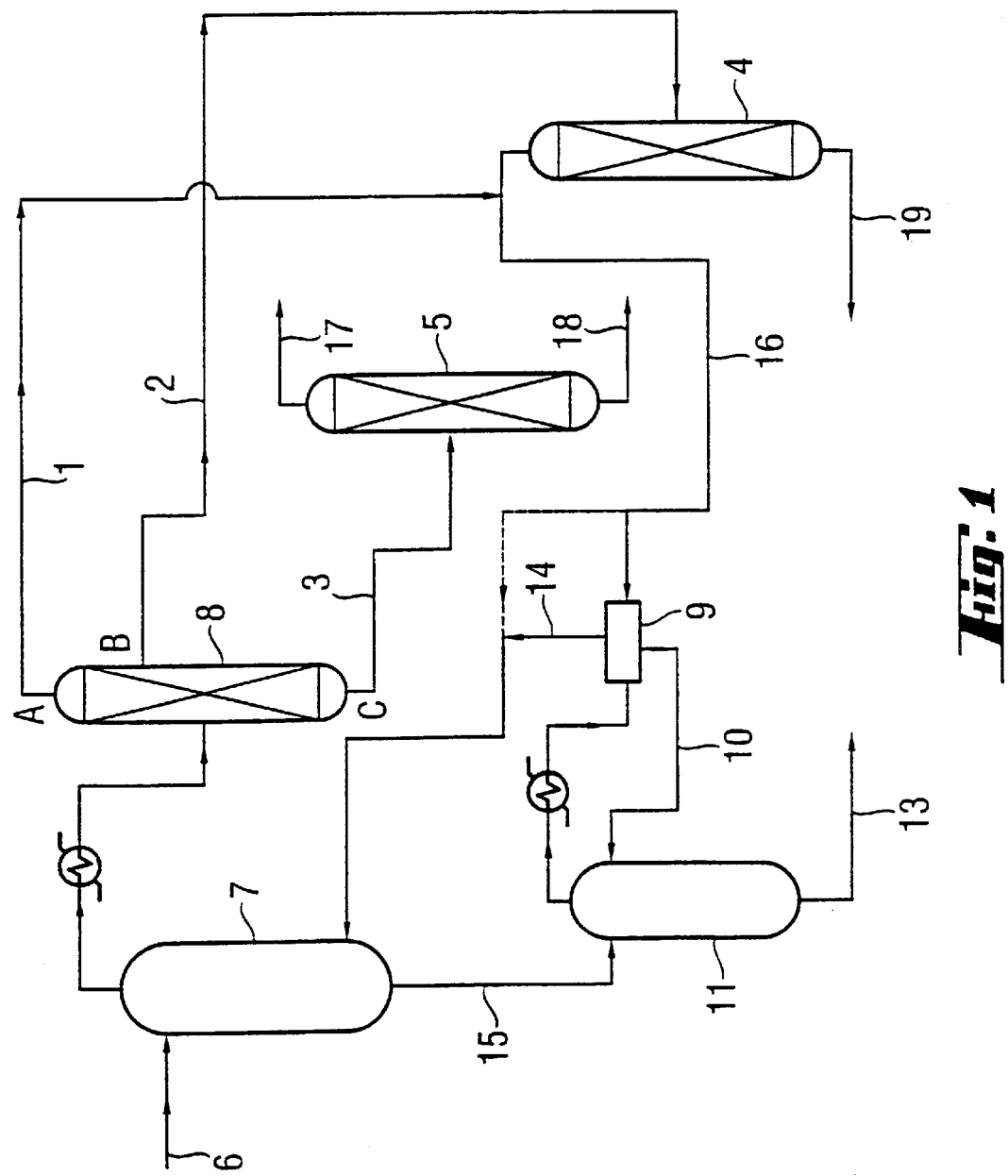
FIG. 1 shows in a first step (extraction) of the process of the invention, that the crude acid feed comprising varying proportions of acetic acid, formic acid, water and high boilers is fed to an extractor and is brought into contact with a solvent.

In the first step (extraction) of the process of the invention (FIG. 1), the crude acid feed comprising varying proportions of acetic acid, formic acid, water and high boilers is fed to an extractor (7) and brought into contact with a solvent. The extractor (7) can have a single-stage or preferably multistage configuration. The solvent stream can, in this process, be directed in the direction of flow of the crude acid or preferably be conveyed in countercurrent to the crude acid. Solvents which can be used here are ethers, esters, ketones, alcohols, saturated, unsaturated and cyclic hydrocarbons having from 4 to 8 carbon atoms and their mixtures, preferably ethers and esters having from 4 to 7 carbon atoms, particularly preferably methyl tert-butyl ether, diisopropyl ether, di-n-propyl ether, ethyl butyl ether, ethyl acetate and isopropyl acetate, in a mixing ratio to crude acid of from 0.5 to 20, preferably from 1 to 5, particularly preferably from 1.5 to 3.5 (ratio volume/volume). The extraction can take place in a temperature and pressure range in which the extraction solvent and the crude acid are present in liquid form and as separate phases, i.e. with a miscibility gap. Preference is given to a temperature range from 0° C. to 60° C. and a pressure range from $1*10^5$ to $20*10^5$ Pa.

The raffinate obtained from the extractor (7) is fed via line (15) to the solvent stripping column (11) where pure water is taken off (line (13)) at the bottom. The product from the top of the solvent stripping column is fed to a phase separator (9). The aqueous phase obtained there goes via line (10) back to the top of the solvent stripping column (11), while the organic phase is recirculated via line (14) to the extractor (7).

The extract taken off from the extractor (7), comprising solvent, acetic acid, formic acid, water and high boilers, is conveyed from the extractor (7) to a solvent distillation column (8). In this column, the extract is fractionated into three substreams by distillation.

One substream (mixture (A)) comprising the major part of the solvent and residues of acid and water is taken off at the top of the column and fed into the phase separator (9) of the solvent stripping column (11). Alternatively, this substream can also be recirculated directly, bypassing the phase separator, to the extractor (7).

A further substream (mixture (B)) comprising the components water, solvent and formic acid is taken off in vapor form from the solvent distillation column (8) via a side offtake and conveyed to a formic acid distillation column (4) from the bottom of which pure formic acid is taken off via line (19). At the top of the column (4), a mixture of solvent and water is taken off and conveyed via line (16) to the phase separator (9). There, the organic phase is separated from the water and recirculated via line (14) to the extractor (7).

The remaining substream (mixture (C)) comprising acetic acid and high boilers is separated off at the bottom of the solvent distillation column (8) and conveyed to an acetic acid distillation column (5) for fractionation into pure acetic acid and high boilers. The acetic acid is taken off at the top via line (17) and the high boilers are separated off at the bottom of the column via line (18).

In the embodiment described, taking off the feed in vapour form by means of a side offtake on the solvent column (8) and feeding it in vapour form into the formic acid distillation column leads to an energy saving compared to systems without such an arrangement.

Figure 2:
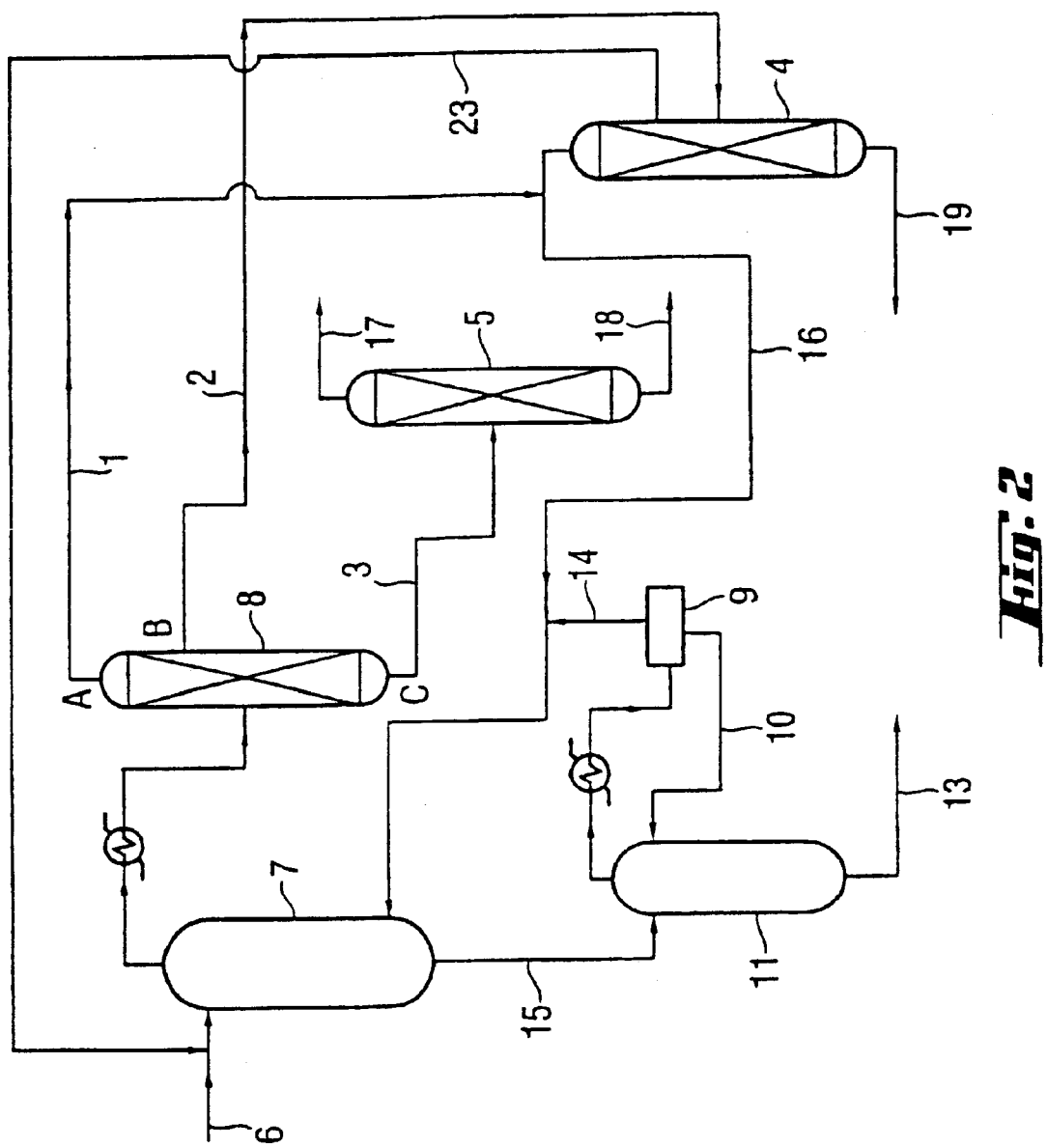
FIG. 2 shows another embodiment of the process of the invention, in which the formic acid distillation column (4) has an additional side offtake.

In a particular embodiment (FIG. 2) of the above-described process of the invention, the formic acid distillation column (4) has an additional side offtake. From this, to make the separation easier, a small substream of a mixture comprising water, formic acid and solvent is taken off and collected separately or recirculated via line (23) to the crude acid inlet (6) or another point on the extractor (7). At the bottom of the column (4), pure formic acid is taken off via line (19). The mixture comprising solvent, water and traces of acid obtained at the top of the formic acid distillation column (4) is recirculated via line (16) to the extractor (7). A particular advantage of this embodiment is that the provision of the side offtake on the column reduces the energy requirement for the formic acid distillation.

In a further particular embodiment (FIG. 3) of the process of the invention, the substream (mixture (B)) comprising a mixture of water, solvent and formic acid which is taken off in gaseous form from the solvent column (8) via a side offtake is condensed and passed to the phase separator (20) before being introduced into the formic acid distillation column (4). The organic phase which has been separated off is pumped via line (22) into the formic acid distillation column (4) which operates at a superatmospheric pressure of from $1*10^5$ to $10*10^5$ Pa. At the bottom of this column, pure formic acid is taken off via line (19). The mixture comprising solvent, water and traces of acid obtained at the top of this column is conveyed via line (16) to the phase separator (9) of the solvent stripping column (11). Alternatively, this substream can also be recirculated directly, bypassing the phase separator, to the extractor (7). The aqueous phase from the phase separator (20) is collected separately or recirculated via line (21) to the crude acid inlet (6) or another point on the extractor (7).

A particular advantage of this embodiment is a further energy saving. As a result of the condensation of the substream (mixture (B)) taken off at the side offtake of the solvent distillation column (8) and the subsequent phase separation, a major part of the water can be separated off without energy-intensive distillation. In addition, a higher operation pressure and a lower water content in the feed to the formic acid distillation column (4) makes the isolation of pure formic acid easier.

In a further particular embodiment (FIG. 4) of the process of the invention, the substream (mixture (B)) comprising a mixture of water, solvent and formic acid taken off in gaseous form from the solvent column (8) via a side offtake is condensed (analogous to FIG. 3) and fed to the phase separator (20) prior to being introduced into the formic acid distillation column (4). The organic phase formed is pumped via line (22) to the formic acid distillation column, (4) operated under a superatmospheric pressure of from $1*10^5$ to $10*10^5$ Pa. At the bottom of this column, pure formic acid is taken off via line (19). The mixture of solvent, water and traces of acid obtained at the top of this column is recirculated directly via line (16) to the extractor (7). In this embodiment, the formic acid distillation column (4) additionally has a side offtake (23). There, to aid the separation, a small substream of a mixture comprising water, formic acid and solvent is taken off and collected or recirculated to the crude acid inlet (6) or another point on the extractor (7). The aqueous phase from the phase separator (20) is likewise collected via line (21) or recirculated to the crude acid inlet (6) or another point on the extractor (7).

A particular advantage of this embodiment is that the provision of the side offtake on the column (4) additionally reduces the energy requirement in the formic acid distillation. At the same time, the condensation of the substream (mixture (B)) taken off at the side offtake of the solvent distillation column (8) and the subsequent phase separation means that a major part of the water is separated off without energy-intensive distillation. The reduced water content in the feed to the formic acid distillation column (4) additionally aids the isolation of the pure formic acid.

The following examples illustrate the process of the invention with reference to the figures:

DETAILED DESCRIPTION OF PREFERRED EMBODIMENTS

EXAMPLE 1

In an apparatus corresponding to FIG. 1, a crude acid stream comprising 12.7 kg/h of acetic acid, 2.9 kg/h of formic acid, 49.7 kg/h of water and 0.2 kg/h of high boilers was fed via line (6) to the extractor (7) (countercurrent extraction column with stationary stainless steel packing, organic phase dispersed). In steady-state operation, the solvent return stream via line (14) to the extractor (7) was adjusted so that it comprised 150 kg/h of methyl tert-butyl ether (MTBE), 6 kg/h of water and 0.02 kg/h of formic acid. The extract stream leaving the extractor (7) was composed of 150 kg/h of MTBE, 12.7 kg/h of acetic acid, 6.0 kg/h of water, 2.9 kg/h of formic acid and 0.2 kg/h of high boilers.

The solvent distillation column (8) and the pure acetic acid column (5) were operated at a pressure of approx. $1*10^5$ Pa. The pure formic acid column (4) was operated at a pressure of approx. $5*10^5$ Pa.

At the bottom of the solvent column (8), a substream (mixture (C)) comprising 12.7 kg/h of acetic acid and 0.2 kg/h of high boilers was discharged at a temperature of 121° C. via line (3). From the side offtake of this column, a substream (mixture (B)) comprising 18.4 kg/h of MTBE, 0.02 kg/h of acetic acid, 2.9 kg/h of formic acid and 3.0 kg/h of water was discharged at a temperature of 84° C. At the top of this column, a substream (mixture (A)) comprising 131.6 kg/h of MTBE, 3.0 kg/h of water and 0.01 kg/h of formic acid was discharged at a temperature of 56° C.

At the bottom of the acetic acid column (5), 0.2 kg/h of high boilers was taken off at a temperature of 181.7° C. via line (18). At the top of the acetic acid column (5), 12.7 kg/h of acetic acid were taken off at a temperature of 117.6° C. via line (17).

At the top of the pure formic acid column (4), a stream comprising 18.4 kg/h of MTBE, 0.01 kg/h of formic acid and 3.0 kg/h of water was taken off at a temperature of 117° C. At the bottom of the formic acid column (4), 0.02 kg/h of acetic acid and 2.9 kg/h of formic acid were taken off at a temperature of 164° C. via line (19).

Fractionation of the crude acid mixture into 2.9 kg/h of 99.28% purity by weight formic acid and 12.7 kg/h of 99.99% purity by weight acetic acid required, without preheating of the feed upstream of the distillation columns, the following energy input:

bottom heating of the solvent distillation column (8): 35 kW bottom heating of the formic acid column (4): 15 kW bottom heating of the pure acetic acid column (5): 4.5 kW Total: 54.5 kW corresponds to 3.5 kW per kg of acid.

EXAMPLE 2

Figure 3:
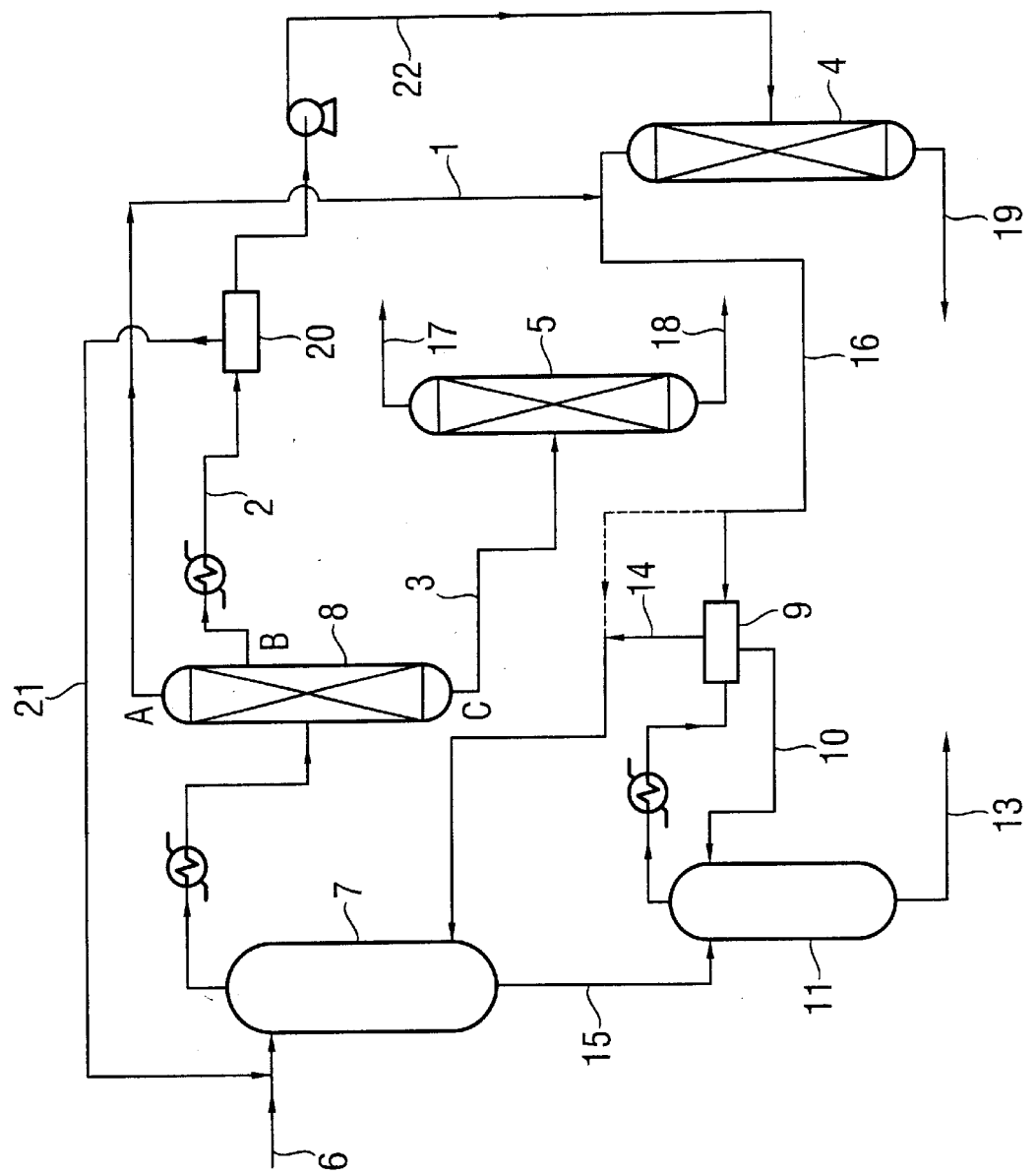
FIG. 3 shows a further embodiment of the process of the invention, in which the substream (mixture (B)) comprising a mixture of water, solvent and formic acid is taken off in gaseous form from the solvent column via a side offtake and is condensed and passed to the phase separator before being introduced into the formic acid distillation column.
Figure 4:
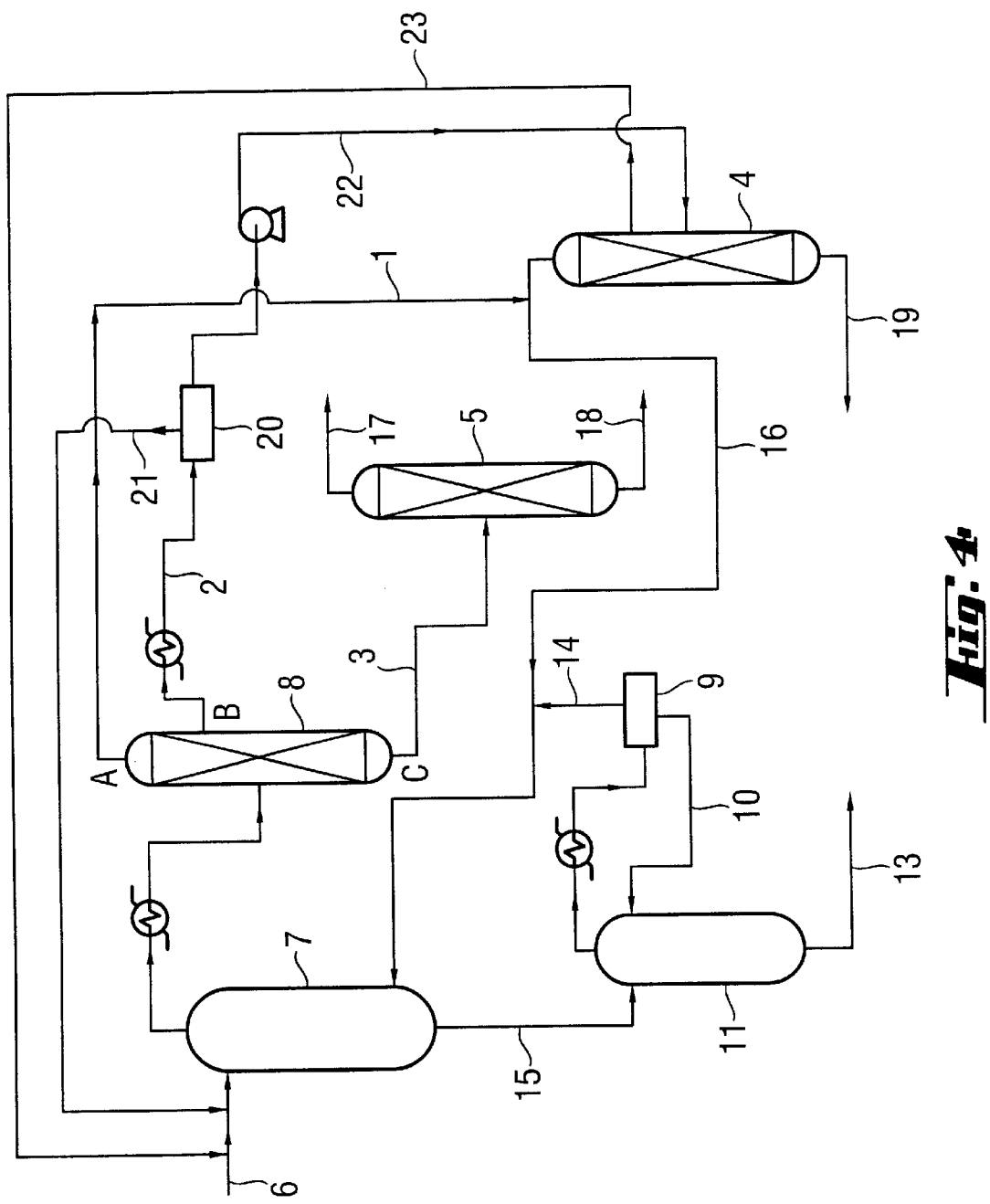
FIG. 4 shows another further embodiment of the process of the invention, in which the substream (mixture (B)) comprising a mixture of water, solvent and formic acid is taken off in gaseous form from the solvent column via a side offtake and is condensed (analogous to FIG. 3).

In an apparatus corresponding to the embodiment shown in FIG. 3, a crude acid stream comprising 12.7 kg/h of acetic acid, 2.9 kg/h of formic acid, 47.8 kg/h of water and 0.2 kg/h of high boilers was fed via line (6) to the extractor (7) (countercurrent extraction column with stationary stainless steel packing, organic phase dispersed). In steady-state operation, the solvent return stream via line (14) to the extractor (7) was adjusted so that it comprised 150.0 kg/h of methyl tert-butyl ether (MTBE), 4.0 kg/h of water and 0.03 kg/h of formic acid. The extract stream leaving the extractor (7) was composed of 150.0 kg/h of MTBE, 12.7 kg/h of acetic acid, 6.0 kg/h of water, 2.9 kg/h of formic acid and 0.2 kg/h of high boilers.

The solvent distillation column (8) and the pure acetic acid column (5) were operated at a pressure of approx. $1*10^5$ Pa. The pure formic acid column (4) was operated at a pressure of approx. $5*10^5$ Pa.

At the bottom of the solvent column (8), the mixture (C) comprising 12.7 kg/h of acetic acid and 0.2 kg/h of high boilers was discharged at a temperature of 121° C. via line (3). From the side offtake of the column (8), a mixture (B) comprising 18.4 kg/h of MTBE, 0.02 kg/h of acetic acid, 2.9 kg/h of formic acid and 3.0 kg/h of water was discharged at a temperature of 84° C. At the top of this column, a mixture (A) comprising 131.6 kg/h of MTBE, 3.0 kg/h of water and 0.01 kg/h of formic acid was discharged at a temperature of 56° C. Mixture (B) was condensed and conveyed via line (2) to the phase separator (20). The phases formed were subsequently separated. The organic phase comprising 18.2 kg/h of MTBE, 1.0 kg/h of water, 0.01 kg/h of acetic acid and 2.5 kg/h of formic acid was discharged via line (22) and introduced as feed into the formic acid column (4). The aqueous phase comprising 2.0 kg/h of water, 0.01 kg/h of acetic acid and 0.4 kg/h of formic acid was collected separately.

At the bottom of the acetic acid column (5), 0.2 kg/h of high boilers was taken off at a temperature of 181.7° C. via line (18). At the top of the acetic acid column (5), 12.7 kg/h of acetic acid were taken off at a temperature of 117.6° C. via line (17).

At the top of the pure formic acid column (4), a stream comprising 18.2 kg/h of MTBE, 0.02 kg/h of formic acid and 1.0 kg/h of water was taken off at a temperature of 115° C. via line (16). At the bottom of the formic acid column (4), 0.01 kg/h of acetic acid and 2.5 kg/h of formic acid were taken off at a temperature of 164° C. via line (19).

Fractionation of the crude acid mixture into 2.5 kg/h of 99.65% purity by weight formic acid and 12.7 kg/h of 99.99% purity by weight acetic acid required, without preheating of the feed upstream of the distillation columns, the following energy input:

bottom heating of the solvent distillation column (8): 35 kW bottom heating of the formic acid column (4): 7 kW bottom heating of the pure acetic acid column (5): 4.5 kW Total: 47 kW corresponds to 3.1 kW per kg of acid.

In contrast, fractionation of the crude acid mixture by methods of the prior art requires an energy input of at least 4 kW per kg of acid and gives a contaminated (with water, acetic acid, entrainer such as benzene or chlorinated hydrocarbons) formic acid.

What is claimed is:

1. A process for the separation and purification of an aqueous mixture comprising main components acetic acid, formic acid and high boilers, comprising the steps of feeding a raffinate stream containing a major part of water to a solvent stripping column (11) for removal of the water;

conveying an extract stream to a solvent distillation column (8) having a top and a bottom and from which, in a first step, a mixture (A) comprising a major part of the solvent is separated off via the top and a mixture (B) comprising formic acid, water and solvent is separated off at a side offtake and a mixture (C) comprising acetic acid and high boilers is separated off via the bottom;

feeding the mixture (B) to a formic acid distillation column (4) and feeding the mixture (C) to an acetic acid distillation column (5); and subsequently isolating purified acetic acid at a top of the acetic acid distillation column (5), isolating purified formic acid at a bottom of the formic acid distillation column (4) and at a top taking off a mixture of solvent and water which, together with the mixture (A) after separating off the water present, is recirculated to an extractor (7).

2. The process as claimed in claim 1, comprising operating the extractor in at least one stage.

3. The process as claimed in claim 1, wherein a solvent circuit in the extractor runs concurrent to crude acid.

4. The process as claimed in claim 1, wherein the solvent used is selected from the group consisting of saturated hydrocarbons having from 4 to 8 carbon atoms, unsaturated hydrocarbons having from 4 to 8 carbon atoms, cyclic hydrocarbons having from 4 to 8 carbon atoms, and mixtures thereof.

5. The process as claimed in claim 1, wherein the solvent used is at least one compound selected from the group consisting of ethers, esters, ketones, hydrocarbons, alcohols, and mixtures thereof.

6. The process as claimed in claim 1, wherein the solvent used is at least one compound selected from the group consisting of methyl tertbutyl ether, diisopropyl ether, di-n-propyl ether, ethyl butyl ether, ethyl acetate, isopropyl acetate, and mixtures thereof.

7. The process as claimed in claim 1, comprising carrying out the extraction at temperatures of 0° C. to 60° C. and pressures of $1*10^5$ to $20*10^5$ Pa.

8. The process as claimed in claim 1, wherein there is a mixing ratio (volume/volume) of solvent to crude acid of from 0.5 to 20.

9. The process as claimed in claim 1, further comprising providing the formic acid column (4) with a side offtake from which a substream is taken off.

10. The process as claimed in claim 9, further comprising recirculating the substream from the side offtake of the formic acid column to the extractor.

11. The process as claimed in claim 1, wherein a substream mixture (B) comprising the mixture of water, solvent and formic acid taken off in gaseous form from the solvent distillation column (8) via the sides offtake is, prior to introduction into the formic acid distillation column (4), condensed and fed to a phase separator (20);

pumping an organic phase formed into the formic acid distillation column (4) operated under superatmospheric pressure; and feeding a mixture comprising solvent, water and traces of acid obtained at a top of said column (4) to a phase separator (9) of the solvent stripping column (11).

12. The process as claimed in claim 11, further comprising recirculating an aqueous phase from the phase separator (20) to the extractor (7).

13. A process for the separation and purification of an aqueous mixture comprising main components acetic acid, formic acid and high boilers, comprising the steps of feeding a raffinate stream containing a major part of water to a solvent stripping column (11) for removal of the water;

conveying an extract stream to a solvent distillation column (8) having a top and a bottom and from which, in a first step, a mixture (A) comprising a major part of the solvent is separated off via the top and a mixture (B) comprising formic acid, water and solvent is separated off at a side offtake and a mixture (C) comprising acetic acid and high boilers is separated off via the bottom;

feeding the mixture (B) to a formic acid distillation column (4) and feeding the mixture (C) to an acetic acid distillation column (5);

subsequently isolating purified acetic acid at a top of the acetic acid distillation column (5), isolating purified formic acid at a bottom of the formic acid distillation column (4) and at a top taking off a mixture of solvent and water which, together with the mixture (A) after separating off the water present, is recirculated to an extractor (7);

providing the formic acid column (4) with a side offtake from which a substream is taken off;

recirculating the substream from the side offtake of the formic acid column to the extractor;

wherein a substream of mixture (B) comprising the mixture of water, solvent and formic acid taken off in gaseous form from the solvent distillation column (8) via the sides offtake is, prior to introduction into the formic acid distillation column (4), condensed and fed to a phase separator (20);

pumping an organic phase formed into the formic acid distillation column (4) operated under superatmospheric pressure; and feeding a mixture comprising solvent, water and traces of acid obtained at a top of said column (4) to a phase separator (9) of the solvent stripping column (11); and recirculating an aqueous phase from the phase separator (20) to the extractor (7).

* * * * *

UNITED STATES PATENT AND TRADEMARK OFFICE
CERTIFICATE OF CORRECTION

PATENT NO. : 6,695,952 B1
DATED : February 24, 2004
INVENTOR(S) : Rüdinger et al.

It is certified that error appears in the above-identified patent and that said Letters Patent is hereby corrected as shown below:

<u>Title page,</u>
Item [75], Inventors, the name of the fifth inventor should read -- Barbara Wild --.

Signed and Sealed this

Twentieth Day of July, 2004

JON W. DUDAS
*Acting Director of the United States Patent and Trademark Office*